United States Patent [19]
Rehner et al.

[11] Patent Number: 4,716,119
[45] Date of Patent: Dec. 29, 1987

[54] CONTROL SERUM AND PROCESS THEREFOR

[75] Inventors: Helmut Rehner, Weilheim; Peter Roeschlau, Seeshaupt, both of Fed. Rep. of Germany

[73] Assignee: Boehringer Mannheim GmbH, Mannheim, Fed. Rep. of Germany

[21] Appl. No.: 917,240

[22] Filed: Oct. 7, 1986

Related U.S. Application Data

[60] Division of Ser. No. 663,832, Oct. 23, 1984, abandoned, which is a continuation of Ser. No. 350,867, Feb. 22, 1982, abandoned.

[30] Foreign Application Priority Data

Feb. 25, 1981 [DE] Fed. Rep. of Germany ....... 3107060

[51] Int. Cl.$^4$ .................................... G01N 31/00
[52] U.S. Cl. ....................... 436/16; 436/17; 436/18

[56] References Cited

U.S. PATENT DOCUMENTS

| | | | |
|---|---|---|---|
| 2,094,931 | 10/1937 | Schultze | 436/13 X |
| 2,871,266 | 1/1959 | Riley | 260/584 |
| 3,260,648 | 7/1966 | Fox | 167/84 |
| 3,506,828 | 4/1970 | Hansen | 250/71.5 |
| 3,552,928 | 1/1971 | Fetter | 23/253 |
| 3,629,142 | 12/1971 | Marbach | 252/408 |
| 3,955,925 | 5/1976 | Proksch et al. | 436/13 |
| 3,997,470 | 12/1976 | Monte et al. | 252/408.1 |
| 4,001,142 | 1/1977 | Turner | 252/408.1 |
| 4,011,045 | 3/1977 | Bonderman | 436/13 |
| 4,056,468 | 11/1977 | Breiter et al. | 436/13 X |
| 4,121,905 | 10/1978 | Maurukas | 23/230 B |
| 4,127,502 | 11/1978 | Li Mutti et al. | 252/408.1 |
| 4,175,074 | 11/1979 | Deshmukh | 260/121 |
| 4,184,848 | 1/1980 | Batz | 436/175 |
| 4,189,401 | 2/1980 | Louderback | 252/408.1 |
| 4,198,206 | 4/1980 | Ryan | 436/18 |
| 4,216,117 | 8/1980 | Proksch et al. | 436/13 |
| 4,239,649 | 12/1980 | Gindler et al. | 252/408.1 |
| 4,264,471 | 4/1981 | Briggs | 252/408.1 X |
| 4,389,490 | 6/1983 | Crews et al. | 436/10 X |

FOREIGN PATENT DOCUMENTS

| | | | |
|---|---|---|---|
| 2243014 | 9/1972 | Fed. Rep. of Germany ... | 252/408.1 |
| 2327894 | 6/1973 | Fed. Rep. of Germany ...... | 436/175 |

OTHER PUBLICATIONS

Bonderman, et al., "Addition of Triglyceride...", Clin. Chem. 22/8, 1299-1301 (1976).
Proksch, et al., "Use of a Cholesterol-Rich...", Clin. Chem. 22/8, 1302-1305 (1976).
Proksch, et al., "Preparation of Optically Clear...", Clin. Chem. 22/4, 456-460, (1976).

*Primary Examiner*—Donald P. Walsh
*Assistant Examiner*—T. J. Wallen
*Attorney, Agent, or Firm*—Felfe & Lynch

[57] ABSTRACT

Control serum containing (1) at least one compound of the formula:

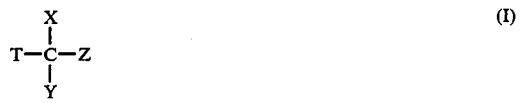

(I)

in which
  T is hydrogen or methyl, hydroxymethyl or methoxymethyl
  X is hydrogen hydroxymethyl or methyl when Y is hydroxyl, hydroxymethyl or $NR_2$;
  Y is hydrogen, hydroxyl, hydroxylmethyl or $NR_2$ and
  Z is hydroxyl or an $-O-CH_2-CH_2OH$ group when Y is hydrogen or hydroxymethyl, or Z is hydroxymethyl or a carboxyl derivative or
  T is ethyl or isopropyl,
  X is hydrogen, or methyl, hydroxymethyl or methoxy,
  Y is hydroxy, hydroxymethyl or $NR_2$ and
  Z is a carboxyl derivative;

each R independently is hydrogen or an alkyl group with 1 to 2 carbon atoms optionally containing a hydroxy group and/or (2) at least one compound of the formula $$HO(CH_2-CH_2-O)_nH, \qquad (II)$$

in which n is an integer from 2 to 8, in an amount sufficient to reduce turbidities in reconstituted serum after previous lyophilization.

1 Claim, No Drawings

CONTROL SERUM AND PROCESS THEREFOR

This application is a divisional of application Ser. No. 663,832 filed Oct. 23, 1984 (abandoned) which in turn is a continuation of application Ser. No. 350,867 filed Feb. 22, 1982 (abandoned).

The present invention relates to a control or calibration serum. More specifically the invention relates to such a serum having a reduced tendency to turbidity formation upon reconstitution after previous lyophilization. In additional aspect, the invention is concerned with a process for the preparation of serum.

Natural sera of human or animal origin and serum-like artificial compositions with a precisely adjusted content of various serum components of interest are referred to as control or calibration sera which are intended for the calibration or control of processes for the determination of serum components.

The use of human and animal sera or of compositions of a similar kind, which are derived from sera or plasmas, is known for the preparation of control and calibration sera. The adjustment of the concentration or activity of clinically relevant parameters (substrates, electrolytes, enzymes, hormones and the like) to desired values is also known (Proc. Royal Soc. Med., 68, 624–629/1975).

Control or calibration sera which contain sensitive substances, such as enzymes, bilirubin, lipoproteins, hormones and the like, must, for reasons of storage stability, be kept deep-frozen or, after lyophilization be kept at refrigerator temperature.

Due to the process of lyophilization the solubility of some components is reduced and, consequently, in the reconstituted sample, produce a turbidity which occurs in particular when the control or calibration serum has a comparatively high lipid concentration.

It is well known that turbidities are very undesirable in control and calibration sera. Thus, problems can occur in many spectrophotometric methods if the turbidity of the sample is not taken into account by means of a corresponding blank.

The turbidity of the control or calibration sera cause special problems particularly in the case of determinations of enzyme activities which depend upon the NADH/NAD+ measurement and are carried out, for example, at 340 nm.

In the case of measurements at 340 nm, the turbidity of the sample (control or calibration serum) can additionally so strongly increase the in any case already high extinction of NADH in the reaction mixture that the resulting extinction measurements must be carried out in an extinction range of the photometer which is no longer precise. This means that the measurements become less precise (i.e. the coefficient of variation (CV) of the determinations is greater). Furthermore, the results obtained depend greatly upon the quality of the photometer used.

Attempts have already been made to solve the turbidity problem in many ways:

(1) By shock freezing of the control or calibration sera in granulate form in an appropriate freezing bath, lyophilization of the frozen granulates in bulk form and dry filling of the lyogranulate obtained by weighing out into appropriate flasks (Federal Republic of Germany Patent Specification No. 22 43 014).

This process has the advantage that, without manipulation of the control/calibration serum raw material, a product is to be obtained of relatively low turbidity. However, a disadvantage of this technique is that it requires a large investment and the problem of filling lyogranulate into containers has, at present, not been satisfactorily solved, i.e. it still cannot be carried out technically on a large scale.

(2) By separation from the sera of the $\beta$-lipoproteins, which are mainly responsible for the turbidity, and a possibly subsequent spiking up of cholesterol with an appropriate lipoprotein fraction ($\alpha$-lipoprotein) or of triglyceride with trioctanoin in the presence of Triton X 114 (Clin. Chem., 22, 456–460, 1299–1305/1976).

An important disadvantage of this process is that the precipitation of the $\beta$-lipoproteins by means of $Ca^{2+}$/dextran sulphate and separation thereof considerably raises the price of the serum raw material being made.

A subsequent spiking up of the matrix with an appropriate lipoprotein fraction for increasing the cholesterol concentration is admittedly possible and only results in a moderate increase of turbidity (in the case of 300 mg. cholesterol/dl E 157 0.7) but a simultaneous increase of the triglyceride concentration is not possible in this way.

The addition of detergent (Triton X 114) is also critical since test disturbances and/or enzyme inactivations are hereby to be expected.

(3) By the addition of sugars, sugar alcohols and aminosugars to the control or calibration sera, which reduce or prevent the denaturing of the lipoproteins during lyophilization (Federal Republic of Germany Patent Specification No. 28 25 391).

In comparison with Processes (1) and (2), this process has the advantage that the conventional techniques can be employed and a working over of the raw material is avoided.

Disadvantages of this process are that in some cases large amounts of "stabilizer" must be added, the properties of the reconstituted control/calibration serum thereby being changed (e.g. viscosity), and that the stabilizers used are "physiological" materials which can disturb certain tests (e.g. the disturbance of glucose determinations using the HK/G6P-DH method by glucose, glucosamine and fructose) or which can possibly change in the serum (e.g. hydrolysis of sucrose or lactose by $\alpha$-glucosidase, invertase or $\beta$-galactosidase since these enzymes can get into the control/calibration serum as so-called enzyme impurities when spiking up enzymes).

The turbidity (extinction of an undiluted sample reconstituted with water or diluent, measured against water at Hg 546 nm) of a sample produced by Process (1) (shock freezing) is about 0.5.

The turbidity of control/calibration sera prepared by conventional processes from normal human serum (lyophilization of a sample frozen at $-30°$ C. to $-50°$ C.) is 0.8 to 1.3.

Control/calibration sera which are prepared by Process (2) have a turbidity of about 0.3. However, after separation of the $\beta$-lipoproteins, the content of triglyceride or cholesterol is very low.

Therefore, it is an object of the present invention to provide a calibration serum or control serum which has a reduced tendency to turbidity formation but does not possess the disadvantages of the known solutions for this problem.

We have now found, and upon this depends the present invention, that less turbid and more homogeneous control/calibration sera can be prepared with the previously used technique when certain organic compounds, which are not sugars, are added before lyophilization to compositions based upon human or animal serum or some other composition derived from serum or plasma.

Thus, according to the present invention, there is provided a control or calibration serum, containing at least one compound of the general formula:

(I)

in which T is a hydrogen atom or a methyl-, hydroxymethyl- or methoxymethyl group, X is a hydrogen atom a hydroxymethyl group or a methyl group, if Y is a hydroxyl group, a hydroxymethyl group or an $NR_2$ group, Y is a hydrogen atom, a hydroxyl group or a hydroxymethyl or $NR_2$ group and Z a hydroxyl group or an —O—$CH_2$—$CH_2OH$ group, if Y is a hydrogen atom or a hydroxymethyl group, or Z is a hydroxymethyl group or a carboxyl derivative; or T is an ethyl or isopropyl group, X is a hydrogen atom or a methyl-, hydroxymethyl or methoxy group, Y is a hydroxyl group or a hydroxymethyl or $NR_2$ group and Z is a carboxyl derivative and each R, independently of one another, is a hydrogen atom or an alkyl group containing 1 or 2 carbon atoms and optionally containing a hydroxyl group, and/or at least one compound of the general formula:

$HO(CH_2—CH_2—O)_nH$ (II)

in which n is a whole number of from 2 to 8, in an amount which is sufficient to prevent wholly or partly turbidities in reconstituted serum after previous lyophilization.

The expression "carboxyl derivative" is to be understood to mean a carboxylic acid amide or ester or the carboxyl group itself.

An especially strong clearing up effect is displayed by those compounds of general formula (I) which contain carboxylate groups. The fundamental carboxylic acids are neutralised before use according to the present invention.

If, in the control/calibration sera, the electrolyte content is not of importance, the alkali metal or alkaline earth metal salts of the carboxylic acids can be used. If the concentration of the electrolytes is important for the product, then, as base, it is advantageous to use an amine and preferably a tertiary or quaternary amine, for example a carboxylic acid salt of triethanolamine, tetramethylethylenediamine or tetramethylammonium.

The amount which gives a desired improvement of turbidity depends largely upon which compound is used. The effective concentration for normal sera is usually from 0.5 to 10 g./dl. The required amount of added material depends not only on the material itself but is also determined by the matrix and its composition (e.g. by its lipid or protein content) and can, therefore, vary from case to case.

It is also possible to add several substances of the above-defined type to the serum or to the matrix derived from serum. Mutually strengthening or weakening effects can hereby occur.

Examples of compounds which can be used according to the present invention include methanol, sodium acetate, triethanolammonium acetate, tetramethyldiethyleneammonium diacetate, sodium propionate, sodium lactate, alanine, sodium 2,2-bis-(hydroxymethyl)-propionate, N-methyl-diethanolammonium 2,2-bis-(hydroxymethyl)-propionate, 2,2-bis-(hydroxymethyl)-propionamide, sodium 2-hydroxy-2-methylbutyrate, valine, 2-methoxyethanol, triethyleneglycol, tetraethylene glycol and tetramethylammonium acetate.

The present invention is especially appropriate for universal control or calibration sera, i.e. products which can be used for the quality control or for the calibration of automatic analysis apparatus for possibly all clinically relevant serum parameters, such as enzymes, substrates, metabolites, hormones, electrolytes and the like. In the same way, however, the present invention is also useful for control or calibration sera for special purposes in which, for example, the addition of enzymes or hormones can be omitted. Examples for this include a lipid control serum or a lipid calibration serum/lipid calibrator.

According to the present invention, not only does the serum as a whole become more homogeneous but the precision of concentration and activity determinations of the parameters contained in the control/calibration sera is also improved. This means that the stated values for the individual parameters become more certain and that the ascertainment of the stated values by the user of the quality control sera is made easier or that the calibration of apparatus with these calibrators is improved.

The following Examples further explain the present invention.

The reduction of the turbidity is measured as follows: The extinctions are measured at $\lambda = 546$ nm on the undiluted samples reconstituted with water in a 1 cm. cuvette and the extinctions of samples with additive/additives are compared with samples without additive, i.e. controls.

The extinction at this wavelength is preponderantly determined by the turbidity/inhomogeneity of the sample, the light absorption being relatively small. Thus, the light intensity is preponderantly weakened by light scattering effects. The geometry of the measurement arrangement (light path, arrangement of light source and receiver, aperture, cuvette shape and the like) also influence the light intensity weakening caused by light scattering.

The extinctions are measured with a linear spectral photometer (Eppendorf 6115).

Reconstitution or reconstituting of the sample here means the addition of water or of an aqueous solution (diluent) to the lyophilized sample in the amount present before lyophilization

EXAMPLES 1 TO 15

As serum matrix in this experimental series, use is made of pooled human serum from healthy donors. In order better to demonstrate the turbidity-clearing effect of the added substances, the pooled serum was mixed with egg yolk extract in order to increase the concentration of triglycerides in the serum matrix to values of 160 to 270 mg./dl. The cholesterol content of the serum matrix was not changed.

After the addition of the enzymes, substrates, electrolytes or hormones to the serum matrix, there were added to the serum matrix the substances set out in the following Table 1 in the given concentrations. Thereafter, the batches with and without additive were filtered free of microbes (0.2μ membrane filter layer), filled into flasks and lyophilized. After reconstitution with water, the turbidity of the samples was determined.

TABLE 1

| Example | additive | concentration (%) | turbidity $(E_{546})$ n $\geq$ 11 | | | |
|---|---|---|---|---|---|---|
| | | | median | range | $E_{max}$ | $E_{min}$ |
| 1 | methanol | 0 | 0.82 | 0.35 | 1.07 | 0.72 |
| | | 1.5 | 0.60 | 0.07 | 0.63 | 0.56 |
| | | 3.0 | 0.28 | 0.03 | 0.30 | 0.27 |
| 2 | sodium acetate | 0 | 0.87 | 0.23 | 0.91 | 0.78 |
| | | 2 | 0.25 | 0.02 | 0.25 | 0.23 |
| 3 | triethanol-ammonium acetate | 0 | 0.92 | 0.08 | 0.97 | 0.89 |
| | | 5.2 | 0.32 | 0.03 | 0.33 | 0.30 |
| 4 | tetramethyl-diethylene ammonium diacetate | 0 | 0.81 | 0.35 | 1.07 | 0.72 |
| | | 3 | 0.22 | 0.01 | 0.23 | 0.22 |
| 5 | sodium propionate | 0 | 0.87 | 0.23 | 0.91 | 0.78 |
| | | 2.4 | 0.41 | 0.09 | 0.44 | 0.35 |
| 6 | sodium lactate | 0 | 0.87 | 0.23 | 0.91 | 0.78 |
| | | 3 | 0.16 | 0.00 | 0.16 | 0.16 |
| 7 | alanine | 0 | 0.96 | 0.23 | 1.04 | 0.81 |
| | | 3 | 0.40 | 0.05 | 0.44 | 0.39 |
| 8 | sodium 2,2-bis-(hydroxymethyl)-propionate | 0 | 0.96 | 0.09 | 0.98 | 0.89 |
| | | 3.5 | 0.45 | 0.06 | 0.48 | 0.42 |
| 9 | N—methyldiethanolammonium-2,2-bis-(hydroxymethyl)-propionate | 0 | 1.23 | 0.15 | 1.31 | 1.16 |
| | | 5.7 | 0.40 | 0.09 | 0.41 | 0.32 |
| 10 | 2,2-bis-(hydroxymethyl)-propionamide | 0 | 0.96 | 0.09 | 0.98 | 0.89 |
| | | 3 | 0.67 | 0.07 | 0.69 | 0.63 |
| 11 | sodium 2-hydroxy-2-methyl-butyrate | 0 | 0.87 | 0.23 | 0.91 | 0.78 |
| | | 3 | 0.26 | 0.03 | 0.27 | 0.24 |
| 12 | valine | 0 | 0.87 | 0.23 | 0.91 | 0.78 |
| | | 3 | 0.42 | 0.03 | 0.43 | 0.40 |
| 13 | 2-methoxy-ethanol | 0 | 1.01 | 0.11 | 1.06 | 0.95 |
| | | 3 | 0.53 | 0.03 | 0.53 | 0.50 |
| 14 | triethylene glycol | 0 | 1.01 | 0.11 | 1.06 | 0.95 |
| | | 3 | 0.42 | 0.09 | 0.50 | 0.41 |
| 15 | tetraethylene glycol | 0 | 1.01 | 0.11 | 1.06 | 0.95 |
| | | 3 | 0.36 | 0.10 | 0.45 | 0.35 |

The results given above in Table 1 show that in most cases 3% of the added substance suffices in order clearly to reduce the turbidity of the human serum used, methanol, acetate, lactate and 2-hydroxyisobutyrate being especially effective.

Furthermore, it can be seen that the homogeneity of the reconstituted samples is improved by the additives.

The range ($E_{max}-E_{min}$) of the turbidities of at least 11 individual sample flasks is noticeably smaller, i.e. the product as a whole is more uniform or more homogeneous.

EXAMPLES 16 TO 19

For this experimental series, pooled human or bovine serum was used. The lipid content of the human or animal serum matrix is made up to 350 or 150 mg. cholesterol/dl. and 300 or 150 mg. triglyceride/dl., respectively. The following Table 2 summarizes the results obtained.

TABLE 2

| Example | additive | concentration (g./dl) | turbidity ($E_{546}$) median | |
|---|---|---|---|---|
| | | | human serum | bovine serum |
| | none | — | 2.25 | 0.65 |
| 16 | TRA acetate | 5.2 | 1.40 | 0.52 |
| 17 | TMED (acetate)$_2$ | 3.0 | 0.55 | 0.25 |
| 18 | TMED (2-hydroxy-isobutyrate)$_2$ | 4.0 | 0.51 | 0.22 |
| 19 | TMA acetate | 3.8 | 0.31 | 0.18 |

TRA = triethanolammonium
TMED = tetramethylethylenediammonium
TMA = tetramethylammonium It can be seen that by means of a compound of general formula (I) in which Z is COO⁻, together with an appropriate cation, even the turbidity of lipaemic sera can be greatly reduced. The turbidity of Example 19 even agrees with that of the non-lyophilized starting material.

It will be understood that the specification and examples are illustrative but not limitative of the present invention and that other embodiments within the spirit and scope of the invention will suggest themselves to those skilled in the art.

What is claimed is:

1. Process for preparation of a calibration/control serum containing a desired component, comprising preparing an aqueous solution of said component, lyophilizing said solution to form a lyophilizate, reconstituting said lyophilizate with an aqueous medium wherein prior to lyophilization there is added to said solution 0.5 to 10% by weight of the reconstituted solution of a compound selected from the group consisting of sodium acetate, triethanolammonium acetate, tetramethyldiethyleneammonium diacetate, tetramethylethylenediammonium diacetate, tetramethylammonium acetate and combinations thereof, and adding said reconstituted solution to a serum sample.

* * * * *

UNITED STATES PATENT AND TRADEMARK OFFICE
CERTIFICATE OF CORRECTION

PATENT NO. : 4,716,119

DATED : December 29, 1987

INVENTOR(S) : Helmut Rehner, et al.

It is certified that error appears in the above-identified patent and that said Letters Patent is hereby corrected as shown below:

Column 2, line 21: change "157" to -- $Z$ --.

Signed and Sealed this

Sixteenth Day of August, 1988

Attest:

DONALD J. QUIGG

Attesting Officer

Commissioner of Patents and Trademarks